(12) United States Patent
Sharpe (10) Patent No.: US 7,588,936 B2
(45) Date of Patent: Sep. 15, 2009

(54) GENERATING TEETH FROM BONE MARROW CELLS

(75) Inventor: Paul Thomas Sharpe, London (GB)

(73) Assignee: Odontis Ltd., London (GB)

( * ) Notice: Subject to any disclaimer, the term of this patent is extended or adjusted under 35 U.S.C. 154(b) by 0 days.

(21) Appl. No.: 10/546,495

(22) PCT Filed: Feb. 17, 2004

(86) PCT No.: PCT/GB2004/000635

§ 371 (c)(1),
(2), (4) Date: May 23, 2006

(87) PCT Pub. No.: WO2004/074464

PCT Pub. Date: Sep. 2, 2004

(65) Prior Publication Data

US 2007/0003529 A1   Jan. 4, 2007

(30) Foreign Application Priority Data

Feb. 21, 2003 (GB) .................................. 0304030.0

(51) Int. Cl.
*C12N 5/00* (2006.01)
*C12N 5/06* (2006.01)
*C12N 5/08* (2006.01)
(52) U.S. Cl. ...................... 435/373; 435/377; 435/371; 435/372
(58) Field of Classification Search ................. 435/377, 435/373, 372, 371
See application file for complete search history.

(56) References Cited

U.S. PATENT DOCUMENTS 7,497,686 B2   3/2009   Sharpe et al.
7,498,168 B2   3/2009   Sharpe

FOREIGN PATENT DOCUMENTS

EP        1 259 593      8/2001
WO     WO-01/60981     8/2001

OTHER PUBLICATIONS

Tissier-Seta et al, Mech. Dev. 51:3-15, 1995.*
Quint et al, J. Exp. Zoology 288:235-241, 2000.*
Fong et al, J. Dent. Educ. 69:555-570, 2005.*
Teixeira, Clin. Orthod. Res. 2:171-174, 1999.*
Sharpe et al, Sci. American, Aug., 293 (2):34-41, 2005.*
Verfaillie et al, Hematology (Am Soc Hematol Educ Program):369-391, 2002.*
Heikinheimo et al, J. Dent. Res., 76(10): 1625-1636, 1997.*
Baba et al, Archs. Oral Biol. 41(2):215-219, 1996.*
Thomas et al, Arch. Oral Biol. 34(1):27-31, 1989.*
Long, Blood Cells, Molecules, and Diseases 27(3):677-690, 2001.*
Gronthos et al, PNAS 97(25): 13625-13630, 2000.*
Kettunen et al, Dev. Dynamics 219:322-332, 2000.*
Bianchi et al, Wound Rep. Reg. 9:460-466, 2001.*
Cobourne et al., "*Sonic hedgehog* Regulates Epithelial Proliferation and Cell Survival in the Developing Tooth Germ," *J. Dent. Res.*, 80(11): 1974-1979, 2001.
Ferguson et al., "Activin is an essential early mesenchymal signal in tooth development that is required for patterning of the murine dentition," *Genes & Development*, 12: 2636-2649, 1998.
Ferguson et al., "The role of effectors of the activin signalling pathway, activin receptors IIA and IIB, and Smad2, in patterning of tooth development," *Development*, 128: 4605-4613, 2001.
Green et al., "Antagonistic Regulation of *Dlx2* Expression by PITX3 and Msx2: Implications for Tooth Development," *Gene Expression*, 9: 265-281, 2001.
Grigoriou et al., "Expression and regulation of *Lhx6* and *Lhx7*, a novel subfamily of LIM homeodomain encoding genes, suggests a role in mammalian head development," *Development*, 125: 2063-2074, 1998.
Hardcastle et al., "The Shh signalling pathway in tooth development: defects in *Gli2* and *Gli3* mutants," *Development*, 125: 2803-2811, 1998.
Lumsden, "Spatial organization of the epithelium and the role of neural crest cells in the initiation of the mammalian tooth germ," *Development*, 103(Suppl.): 155-169, 1988.
MacKenzie et al., "The homeobox gene Hox 7.1 has specific regional and temporal expression patterns during early murine craniofacial embryogenesis, especially tooth development in vivo and in vitro," *Development*, 111: 269-285, 1991.
Miura et al., "SHED: Stem cells from human exfoliated deciduous teeth," *PNAS*, 100(10): 5807-5812, 2003.
Ringe et al., "Stem cells for regenerative medicine: advances in the engineering of tissues and organs," *Naturwissenschaften*, 89: 338-351, 2002.

(Continued)

*Primary Examiner*—Anne Marie Wehbe
*Assistant Examiner*—Kevin K. Hill
(74) *Attorney, Agent, or Firm*—Fulbright & Jaworski LLP (57) ABSTRACT

The present invention is based on the discovery that teeth primordia can be generated using bone marrow cells and that bone marrow cells may be employed to generate teeth without the need for purification and expansion of a population of cells.

1 Claim, 1 Drawing Sheet

OTHER PUBLICATIONS

Satokata et al., "*Msx1* deficient mice exhibit cleft palate and abnormalities of craniofacial and tooth development," *Nature Genetics*, 6: 348-355, 1994.

Thesleff, "Development biology and building a tooth," *Dental Research*, 34(8): 613-620, 2003.

Thesleff et al., "The Role of Growth Factors in Tooth Development," *International Review of Cytology*, 217: 93-135, 2002.

Thomas et al., "Role of *Dix-1* and *Dix-2* genes in patterning of the murine dentition," *Development*, 124: 4811-4818, 1997.

Aberg et al, "Expression Patterns of Bone Morphogenetic Proteins (Bmps) in the Developing Mouse Tooth Suggest Roles in Morphogenesis and Cell Differentiation," Developmental Dynamics 210, 1997, pp. 383-396.

Acampora, D., et al., Craniofacial, vestibular and bone defects in mice lacking the Distalless related gene Dlx5, Development (1999) 126, 3795-3809.

Asashime et al, "Mesodermal induction in early amphibian embryos by activin A (erthroid differentiation factor)" Roux's Archives of Development Biology 198; 1990, pp. 330-335.

Bagutti et al, "Differentiation of Embryonal Stem Cells into Keratinocytes: Comparison of Wild-Type and B1 Intergrin-Deficient Cells," Development Biology 179, 1996, pp. 184-196.

Bitgood et al, "Hedgehog anf Bmp Genes Are Coexpressed at Many Diverse Sites of Cell-Cell Interaction in th Mouse Embryo," developmental Biology 172, 1995, pp. 126-138.

Chai et al, "Specific Transforming Growth Factor-B Subtypes Regulate Embryonic Mouse Meckel's Cartilage and tooth Development," Development Biology 162, 1994, pp. 85-103.

Chen et al, "Msx1 Controls Inductive Signaling in Mammalian Tooth Morphogenesis," Developmental 122, 1996, pp. 3035-3044.

Conlon et al, "A Primary Requirement for Nodal in the Formation and Maintenance of the Primitive Streak in the Mouse," Development 120, 1994, pp. 1919-1928.

Crossley et al, "The Mouse Fgf8 Gene Encodes a Family of Polypeptides and is Expressed in Regions that Direct Outgrowth and Patterning in the Developing Embryo," Developmental 121, 1995, pp. 439-451.

De Winter et al, "Follistatins Neutralize Activin Bioactivity by Inhibition of Activin Binding to its type II Receptors," Molecular and Cellular Endocrinology 116, 1996, pp. 105-114.

Dohrmann et al, "Expression of Activin mRNA during Early Development in Xenopus laevis," Developmental Biology 157, 1993, pp. 474-483.

Dyson et al, "Activin Signaling has a Necessary Function in Xenopus Early development," Current Biology 7, 1997, pp. 81-84.

Fainsod et al, "The Dorsalizing and Neural Inducing Gene Follistatin is an Antagonist of BMP-4," Mechanism of Development 63, 1997, pp. 39-50.

Feijen et al, "Expression of activin Subunits, Activin Receptors and Follistatin in Postimplantation Mouse Embryos Suggests Specific developmental Functions for Different activins," Development 120, 1994, pp. 3621-3637.

Ferguson et al., "Temporospatial cell interactions regulating mandibular and maxillary arch patterning," Development, 127: 403-412, 2000.

Gage et al, "Dosage Requirement of Pitx2 for Development of Multiple Organs," Development 126, 1999, pp. 4643-4651.

Green et al, "Graded Changes in Dose of a Xenopus Activin A Homologue Elicit Stepwise Transitions in Embryonic Cell Fate," Nature vol. 347, Sep. 1990, pp. 391-394.

Green et al, "Responses of Embryonic Xenopus Cells to Activin and FGF are seperated by Multple Dose Thresholds and Correspond to Distinct Axes of the Mesoderm," Cell vol. 71, Nov. 27, 1992, pp. 731-739.

Heikinheimo et al, "Fgf-8 Expression in the Post-Gastrulation Mouse Suggests roles in the Development of the Face, Limbs and Central Nerous System," Mechanisms of Development 48 48, 1994, pp. 129-138.

Heiko Peters, Annette Neubüser, Klaus Kratochwil and Rudi Balling, Pax9-deficient mice lack pharyngeal pouch derivatives and teeth and exhibit craniofacial and limb abnormalities, Genes & Dev. (1998) 12: 2735-2747.

Hemmati-Brivanlou et al, "A Truncated Activin Receptor Inhibits Mesoderm Induction and Formation of Axial Structures in Xenopus Embryos," Nature vol. 359, Oct. 15, 1992, pp. 609-614.

Hemmati-Brivanlou et al, "Follistatin, an Antagonist of Activin, is expressed in the Spemann Organizer and Dsiplays Direct Neuralizing Activity," Cell Feb. 24, 1994, 283-295.

Hemmati-Brivanlou et al, "Inhibition of Activin Receptor Signaling Promotes Neuralization in Xenopus," Cell, Feb. 24, 1994, pp. 273-281.

Iseki et al, "Sonic Hedgehog is Expressed in Epithelial Cells During Development of Whisker, Hair and Tooth," Biochemical and Biophysical Research Communications 218, 1996, pp. 688-693.

Kettunen et al, "Expression and Function of FGFs -4,-8, and -9 Suggest Functional Redundancy and Repetitive Use as Epithelial Signals During Tooth Morphogensis," developmental Dynamics 211, 1998, pp. 256-268.

Kollar et al., "The Influence of the Dental Papilla on the Development of Tooth Shape in Embryonic Mouse Tooth Germs," J. Embryol. Exp. Morph. vol. 21, Feb. 1969, pp. 131-148.

Kratochwil et al, "Lef1 Expression is Activated by BMP-4 and Regulates Inductive Tissue Interactions in Tooth and Hair Development," Genes & Development 10, 1996, pp. 1382-1394.

Lin et al, "Pitx2 Regulates Lung Asymmetry, Cardiac Positioning and Pituitary and Tooth Morphogenesis," Nature vol. 401, Sep. 16, 1999, pp. 279-282.

Linden GJ. Bone induction in implants of decalcified bone and dentine. J Anat. Apr. 1975;119(Pt2):359-67.

Lu et al, "Function of Rieger Syndrome Gene in Left-Right Asymmetry and Craniofacial Development," Nature vol. 401, Sep. 16, 1999, pp. 276-278.

Masella et al., "Current concepts in the biology of orthodontic tooth movement", Am J Orthod Dentofacial Orthop, 2006, 458-468, vol. 129.

Matzuk et al, "Different Phenotypes for Mice Deficient in Either Activins of Activin Receptor Type II," Nature vol. 374, Mar. 23, 1995, pp. 356-360.

Matzuk et al, "Functional Analysis of Activins During Mammalian Development," Nature vol. 374, Mar. 23, 1995, pp. 354-356.

Matzuk et al, "Multiple Defects and Perinatal Death in Mice Deficient in Follistatin," Nature Nol. 374, Mar. 23, 1995, pp. 360-363.

Michel et al, "Follistatins: More than Follicle-Stimulating Hormone Supressing Proteins," Molecular and Cellular Endocrinology 91, 1993, pp. 1-11.

Mina et al, "The Induction of Odontogenesis in Non-Dental Mesenchyme Combined with Early Murine Mandibular Arch Epithelium," Archs Oral Biol., vol. 32, No. 2, 1987, pp. 123-127.

Morio I. Recombinant study of the mouse molar cervical loop and dental papilla by renal transplantation. Arch Oral Biol. 1985;30(7):557-61. (PUBMED Abstract).

Mucchielli et al, "Mouse Otlx2/RIEG Expression in the Odontogenic Epithelium Precedes Tooth Initiation and Requires Mesenchyme-Derived Signals for Its Maintenance," Developmental Biology 189, 1997, pp. 275-284.

Nakamura et al., "Activin-Binding Protein from Rat Ovary is Follistatin," Science vol. 247, Feb. 1990, pp. 836-838.

Neubuser et al, "Antagonistic Interactions between FGF and BMP Signaling Pathways: A Mechanism for Positioning the Sites of Tooth Formation," Cell vol. 90, Jul. 25, 1997, pp. 247-255.

Ohkubo et al., "Coordinate regulation and synergistic actions of BMP4, SHH and FGF8 in the rostral prosencephalon regulate morphogenesis of the telencephalic and optic vesicles", Neuroscience, Apr. 22, 2002, 1-17, vol. 111(1).

Pownall et al, "eFgF, Xcad3 and Hox genes form a molecular Pathway that Establishes the Anteroposterior Axis in Xenopus," Development 122, 1996, pp. 3881-3892.

Qiu et al, "Role of the Dlx Hoeobox Genes in Proximodistal Patterning of the Branchial Arches: Mutations of Dlx-1, Dlx-2 and Dlx-1 and -2 Alter Morphogenesis of Proximal Skeletal and Soft Tissue Structures Derived from the First and Second Arches," Developmental Biology 185, 1997, pp. 165-184.

Rathjen et al, "Formation of a Primitive Ectoderm like Cell Population, EPL cells, from ES Cells in response to Biologically Derived Factors," Journal of Cell Science 112, 1999, pp. 601-612.

Roberts et al, "Expression of Inhibin/Activin Subunit Messenger Ribonucleic Acids during Rat Embryogenesis," Endocrinology vol. 128, No. 6, 1991, pp. 3122-3129.

Roberts et al, "Expression of Messenger Ribonucleic Acids Encoding the Inhibin/Activin System during Mid-and Late-Gestation Rat Embryogenesis," Endocrinology vol. 134, No. 2, 1994, pp. 914-923.

Sarkar et al, "Inhibition of Wnt Signaling by Exogenous Mfrzb1 Protein Affects Molar Tooth Size," Journal of Dental research vol. 79, No. 4, 2000, pp. 920-925.

Saxen, Lauri. "Effect of Tetracycline on Osteogenesis in Vitro," J. Exp. Zool. 162; pp. 269-294.

Semina et al, "Cloning and Characterization of a Novel-related Homeobox Transcription Factor Gene, RIEG, involved in Rieger Syndrome," Nature Genetics vol. 14, Dec. 1996, pp. 392-399.

Sporn et al., "Peptide Growth Factors and their Receptors II", Springer, Berlin, 1990, 179-210.

Thesleff et al, "Molecular Regulation of Tooth Development," Bone vol. 25, No. 1, Jul. 1999, pp. 123-125.

Thesleff et al, "Regulation of Organogenesis. Common Molecular Mechanisms Regulating the Development of Teeth and Other Organs," Int. J. Dev. Biol. 39, 1995, pp. 35-50.

Thesleff et al, "Signalling Networks Regulating Dental Development," Mechanisms of Development 67, 1997, pp. 111-123.

Thesleff, Irma, "Genetic Basis of Tooth Development and Dental Defects," Acta Odontol Scand 58, 2000, pp. 191-194.

Thomas et al, "The Spatial Localization of Dix-2 During Tooth Development," Connective Tissue Research vol. 32, No. 1-4, 1995, pp. 27-34.

Thomsen et al, "Activins are Expressed Early in Xenopus Embryogenesis an Can Include Axial Mesoderm and Anterior Structures," Cell vol. 63, Nov. 2, 1990, pp. 485-493.

Trowell, O.A., "The Culture of Mature Organs in a Synthetic Medium," Experimental Cell Research 16, p. 118-147, 1959.

Tucker et al, "Transformation of Tooth Type Induced by Inhibition of BMP Signaling," Science vol. 282, Nov. 6, 1998, pp. 1136-1138.

U.S. Appl. No. 10/204,208, filed or 371 (c) Date: Oct. 30, 2002, Title: "Tooth Progenitor Cell and Method for its Production", File History, Requirement for Restriction/Election, Sep. 19, 2005.

U.S. Appl. No. 10/204,208, filed or 371 (c) Date: Oct. 30, 2002, Title: "Tooth Progenitor Cell and Method for its Production", File History, Applicant Arguments/Remarks Made in an Amendment, Nov. 16, 2005.

U.S. Appl. No. 10/204,208, filed or 371 (c) Date: Oct. 30, 2002, Title: "Tooth Progenitor Cell and Method for its Production", File History, Claims, Nov. 16, 2005.

U.S. Appl. No. 10/204,208, filed or 371 (c) Date: Oct. 30, 2002, Title: "Tooth Progenitor Cell and Method for its Production", File History, Response to Election / Restriction Filed, Nov. 16, 2005.

U.S. Appl. No. 10/204,208, filed or 371 (c) Date: Oct. 30, 2002, Title: "Tooth Progenitor Cell and Method for its Production", File History, Non-Final Rejection, Feb. 13, 2006.

U.S. Appl. No. 10/204,208, filed or 371 (c) Date: Oct. 30, 2002, Title: "Tooth Progenitor Cell and Method for its Production", File History, Rule 130, 131 or 132 Affidavits, Jun. 13, 2006.

U.S. Appl. No. 10/204,208, filed or 371 (c) Date: Oct. 30, 2002, Title: "Tooth Progenitor Cell and Method for its Production", File History, Applicant Arguments/Remarks Made in an Amendment, Jun. 13, 2006.

U.S. Appl. No. 10/204,208, filed or 371 (c) Date: Oct. 30, 2002, Title: "Tooth Progenitor Cell and Method for its Production", File History, Claims, Jun. 13, 2006.

U.S. Appl. No. 10/204,208, filed or 371 (c) Date: Oct. 30, 2002, Title: "Tooth Progenitor Cell and Method for its Production", File History, Amendment—After Non-Final Rejection, Jun. 13, 2006.

U.S. Appl. No. 10/204,208, filed or 371 (c) Date: Oct. 30, 2002, Title: "Tooth Progenitor Cell and Method for its Production", File History, Final Rejection, Aug. 23, 2006.

U.S. Appl. No. 10/204,208, filed or 371 (c) Date: Oct. 30, 2002, Title: "Tooth Progenitor Cell and Method for its Production", File History, Applicant Arguments/Remarks Made in an Amendment, Jan. 23, 2007.

U.S. Appl. No. 10/204,208, filed or 371 (c) Date: Oct. 30, 2002, Title: "Tooth Progenitor Cell and Method for its Production", File History, Claims, Jan. 23, 2007.

U.S. Appl. No. 10/204,208, filed or 371 (c) Date: Oct. 30, 2002, Title: "Tooth Progenitor Cell and Method for its Production", File History, Amendment Submitted/Entered with Filing of CPA/RCE, Jan. 23, 2007.

U.S. Appl. No. 10/204,208, filed or 371 (c) Date: Oct. 30, 2002, Title: "Tooth Progenitor Cell and Method for its Production", File History, Rule 130, 131 or 132 Affidavits, Jan. 23, 2007.

U.S. Appl. No. 10/204,208, filed or 371 (c) Date: Oct. 30, 2002, Title: "Tooth Progenitor Cell and Method for its Production", File History, Request for Continued Examination (RCE), Jan. 23, 2007.

U.S. Appl. No. 10/204,208, filed or 371 (c) Date: Oct. 30, 2002, Title: "Tooth Progenitor Cell and Method for its Production", File History, List of references cited by examiner, Feb. 27, 2007.

U.S. Appl. No. 10/204,208, filed or 371 (c) Date: Oct. 30, 2002, Title: "Tooth Progenitor Cell and Method for its Production", File History, Non-Final Rejection, Feb. 27, 2007.

U.S. Appl. No. 10/204,208, filed or 371 (c) Date: Oct. 30, 2002, Title: "Tooth Progenitor Cell and Method for its Production", File History, Examiner Interview Summary Record (PTOL—413), May 16, 2007.

U.S. Appl. No. 10/204,208, filed or 371 (c) Date: Oct. 30, 2002, Title: "Tooth Progenitor Cell and Method for its Production", File History, Rule 130, 131 or 132 Affidavits, Aug. 27, 2007.

U.S. Appl. No. 10/204,208, filed or 371 (c) Date: Oct. 30, 2002, Title: "Tooth Progenitor Cell and Method for its Production", File History, Applicant Arguments/Remarks Made in an Amendment, Aug. 27, 2007.

U.S. Appl. No. 10/204,208, filed or 371 (c) Date: Oct. 30, 2002, Title: "Tooth Progenitor Cell and Method for its Production", File History, Supplemental Response or Supplemental Amendment, Aug. 27, 2007.

U.S. Appl. No. 10/204,208, filed or 371 (c) Date: Oct. 30, 2002, Title: "Tooth Progenitor Cell and Method for its Production", File History, Rule 130, 131 or 132 Affidavits , Aug. 27, 2007.

U.S. Appl. No. 10/204,208, filed or 371 (c) Date: Oct. 30, 2002, Title: "Tooth Progenitor Cell and Method for its Production", File History, Applicant Arguments/Remarks Made in an Amendment, Aug. 27, 2007.

U.S. Appl. No. 10/204,208, filed or 371 (c) Date: Oct. 30, 2002, Title: "Tooth Progenitor Cell and Method for its Production", File History, Claims, Aug. 27, 2007.

U.S. Appl. No. 10/204,208, filed or 371 (c) Date: Oct. 30, 2002, Title: "Tooth Progenitor Cell and Method for its Production", File History, Applicant summary of interview with examiner, Aug. 27, 2007.

U.S. Appl. No. 10/204,208, filed or 371 (c) Date: Oct. 30, 2002, Title: "Tooth Progenitor Cell and Method for its Production", File History, Amendment—After Non-Final Rejection, Aug. 27, 2007.

U.S. Appl. No. 10/204,208, filed or 371 (c) Date: Oct. 30, 2002, Title: "Tooth Progenitor Cell and Method for its Production", File History, Rule 130, 131 or 132 Affidavits, Oct. 9, 2007.

U.S. Appl. No. 10/204,208, filed or 371 (c) Date: Oct. 30, 2002, Title: "Tooth Progenitor Cell and Method for its Production", File History, Rule 130, 131 or 132 Affidavits , Oct. 9, 2007.

U.S. Appl. No. 10/204,208, filed or 371 (c) Date: Oct. 30, 2002, Title: "Tooth Progenitor Cell and Method for its Production", File History, Applicant Arguments/Remarks Made in an Amendment, Oct. 9, 2007.

U.S. Appl. No. 10/204,208, filed or 371 (c) Date: Oct. 30, 2002, Title: "Tooth Progenitor Cell and Method for its Production", File History, Supplemental Response or Supplemental Amendment, Oct. 9, 2007.

U.S. Appl. No. 10/204,208, filed or 371 (c) Date: Oct. 30, 2002, Title: "Tooth Progenitor Cell and Method for its Production", File History, Final Rejection, Jan. 2, 2008.

Vaahtokari et al, "Associations between transforming Growth Factor B1 RNA Expression and Epithelial—mesenchymal Interactions During Tooth Morphogenesis," Development 113, 1991, pp. 985-994.

Vaahtokari et al, "The Enamel Knot as a Signaling Center in the Developing Mouse Tooth," Mechanisms of Development 54, 1996, pp. 39-43.

Vainio et al, "Identification of BMP-4 as a Signal Mediating Secdondary Induction between Epithelial and Mesenchymal Tissues during Early Tooth Develpoment," Cell vol. 75, Oct. 8, 1993, pp. 45-58.

Vale et al, "The Inhibin/Activin Family of Hormones and Growth Factors," Peptide Growth Factors and Their Receptors II Chapter 26, Springer Verlag Berlin, Germany, 1990.

Van Genderen et al, "Development of Several Organs that Require Inductive Epithelial-mesenchymal Interactions is Impaired in LEF-1-deficient Mice," Genes & Development 8, 1994, pp. 2691-2703.

Wilkinson, David, "Whole Mount in Situ Hybridization of Vertebrate Embryos," In situ Hybridization, A Practical Approach Chapter 6, IRL Press, Oxford, UK, 1995.

Yamashita et al, "Osteogenic Protein-1 Binds to Activin Type II Receptors and induces Certain Activin-like Effects," The Journal of Cell biology, vol. 130, 1995, pp. 217-226.

Daily Mail, "Is this the end of dentures?" found online at http://www.dailymail.co.uk/pages/live/articles/health/thehealthnews.html?in_article_id=264317&in_page_id=1797, May 4, 2004.

Daily Mail, "Grow your own new teeth," found online at http://www.dailymail.co.uk/pages/live/articles/health/healthmain.html?in_article_id=310873&in_page_id=1774, Jul. 20, 2004.

MacKenzie et al., "Expression patterns of the homeobox gene, *Hox-8*, in the mouse embryo suggest a role in specifying tooth initiation and shape," *Development*, 115: 403-420, 1992.

Ohazama et al., "Stem-cell-based Tissue Engineering of Murine Teeth," *J. Dent. Res.*, 83(7): 518-522, 2004.

Alison, M.R., et al., *Plastic adult stem cells: will they graduate from the school of hard knocks?*, Journal of Cell Science 116, 599-603 (2003).

Amy J. Wagers, et al., *Little Evidence for Developmental Plasticity of Adult Hematopoietic Stem Cells*, Science 297, 2256 (2002).

Jiang, Y., et al., *Pluripotency of mesenchymal stem cells derived from adult marrow*, Nature 418, 41-49 (2002).

Holden, C., Stem Cells: Controversial Marrow Cells Coming Into Their Own?, Science 315(5813), pp. 760-761 (2007).

Giles, J., The trouble with replication, Nature 442, 344-347 (2006).

Tyler MS, Koch WE. "In vitro development of palatal tissues from embryonic mice. III. Interactions between palatal epithelium and heterotypic oral mesenchyme." J Embryol Exp Morphol. Apr. 1977;38:37-48.

Batouli S, et al. Comparison of stem-cellmediated osteogenesis and dentinogenesis. J Dent Res 82(12): 976-981, 2003.

\* cited by examiner

GENERATING TEETH FROM BONE MARROW CELLS

CROSS-REFERENCE TO RELATED APPLICATIONS

This application is the National Stage of International Application PCT/GB2004/000635 filed Feb. 17, 2004, which claims priority to Great Britain Application No. 0304030.0 filed Feb. 21, 2003.

TECHNICAL FIELD

The invention relates to the production of teeth and in particular the use of cultured bone marrow cells to form teeth.

BACKGROUND OF THE INVENTION

Teeth are essential organs for animal survival and of obvious clinical and/or cosmetic importance. There are many instances where tooth replacement is desirable and current treatments are restricted to artificial prostheses or implants.

Tooth primordia explants can be cultured in vitro allowing a variety of manipulation studies including introduction of genes and/or proteins and tissue recombinations.

Tooth development requires the combination of cells from mesenchymal and epithelial lineages. Development of the mammalian tooth has been recognised as a model system for study of epithelial/mesenchymal interactions during organogenesis. Teeth start to develop early in mammalian embryogenesis (11 days in mice, 6 weeks in humans), from a series of reciprocal interactions between two cell types: oral epithelial cells and neural crest-derived mesenchyme cells.

Inductive signals for tooth development come from the epithelium whereupon the responding mesenchymal cells are programmed to become odontogenic (2).

Odontogenic mesenchymal cells then provide instructive signals for further tooth development (3). The epithelial cells eventually give rise to ameloblasts which are responsible for enamel formation and mesenchyme cells form odontoblasts which produce dentine and cementoblasts.

The identity of these different instructive signals has been revealed by gene expression studies and implantation experiments. FGF8, BMP4 and SHH are established as early instructive signals from the oral epithelium (3). BMP's, FGF's and activin are among the early signals from the mesenchyme (3. 4).

Prior art approaches to the production of tooth primordia have included in vitro tissue recombination. In this approach, two different tissue types are independently dissected from the animal embryo, and these tissues are recombined in the laboratory. Signals from one may then induce formation of tooth primordia in the other. This is a labour intensive process carried out by highly trained workers involving a great deal of surgical skill.

In an alternative approach, Young et al. has showed that cells dissociated from early tooth buds when cultured on a matrix and implanted into an adult animal can form teeth, indicating the presence of both epithelial and mesenchymal dental stem cells (Young, C. S., Terada, S., Vacanti, J. P., Honda, M., Bartlett, J. D., Yelick, P. C. (2002) Tissue engineering of complex tooth structures on biodegradable polymer scaffolds. J. Dent. Res. 81, 695-700).

For human therapeutic purposes the major drawback is the potential problem of graft rejection, thus requiring either immunosuppression of host (recipient), or genetic manipulation of the graft cells to circumvent rejection, and the difficulty of obtaining the cells. Therefore the use of cells derived exclusively from each patient would avoid such rejection problems.

Sharpe (WO 01/60981) showed that cultured embryonic stem cells can give rise to epithelial and mesenchyme lineages, enabling the production of teeth primordia from embryonic stem cells.

Use of stem cells such as embryonic stem cells requires purification and expansion of a population of cells. This involves intricate and highly skilled separation and manipulation techniques. Accordingly, a method for the provision of cells to form tooth progenitor cells for implantation which does not require separation and purification, would greatly facilitate the production of such an implant.

Another problem associated with the use of embryonic stem cells is the limited availability and ease with which the embryonic stem cells can be obtained.

Adult (i.e. non-embryonic) bone marrow cells are known to contain populations of stem cells and pluripotential cells which give rise to (a) haematopoietic cells and (b) stromal (mesenchymal) cells. Haematopoietic cells in the bone marrow, however, do not give rise to non-haematopoietic tissues (Wagers et al). Mesenchymal stem cells give rise to homogeneous differentiated cell types of tissues including bone, cartilage, fat, muscle, tendon, hematopoiesis-supporting stroma, and mesangial tissues, but are not known to be capable of forming organs of composite cell lineages and those that require specific reciprocal tissue interactions, such as teeth whose development requires contributions from more than one cell lineage.

The present invention seeks to overcome at least some of the problems associated with the prior art.

BRIEF SUMMARY OF THE INVENTION

Surprisingly, it has been discovered that teeth and teeth primordia can be generated using bone marrow cells. Accordingly, adult bone marrow cells (i.e. non-embryonic cells which may be obtained from a fully mature animal or an immature animal (e.g. child)) may replace embryonic neural crest-derived mesenchymal cells in the production of tooth progenitor cells and more fully developed structures such as teeth primoridia and teeth.

Since bone marrow cells may be obtained from any individual, the use of such cells in therapeutic tooth formation offers (a) avoidance of problems of graft rejection, and (b) wider accessibility of the pluripotent cell component compared with embryonic stem cells.

Surprisingly, it has also been discovered that bone marrow cells may be employed in the methods of the invention without the need for purification and expansion of a population of cells.

There are various advantages afforded by the present invention.

The present invention is advantageous since it is labour saving.

Further, the present invention is advantageous since it does not involve multiple surgical tissue recombination.

The present invention is advantageous since it does not require the use of embryonic cells and teeth primordia/teeth may be formed entirely from non-embryonic cells.

Advantageously, the methods of the present invention may be employed to form teeth primordia/teeth entirely from non-odontogenic tissues that would not normally form teeth.

It is envisaged that the teachings disclosed herein with respect to tooth development may be used to generate teeth in vitro and ultimately in vivo in an adult oral cavity.

DETAILED DESCRIPTION OF THE INVENTION

According to a first aspect, the invention provides a method of generating a tooth primordium using bone marrow cells, the method comprising:

i) incubating the bone marrow cells in the presence of oral epithelial inductive signals for a time sufficient to produce a tooth progenitor cell;

ii) incubating the tooth progenitor cell in the presence of at least one epithelial cell for a time sufficient to produce a tooth primordium.

Surprisingly, it has also been discovered that bone marrow cells may be employed in the methods of the invention without the need for purification and expansion of a population of cells. Thus, in one embodiment of the invention, the bone marrow cells have not undergone purification for a particular cell type. By "purification for a particular cell type" we refer to any process which increases the proportion of a particular type of bone marrow cell present by removal of one or more other cell types present in the unpurified cell population.

Preferably, the unpurified bone marrow cells have not undergone expansion to increase the proportion of a particular cell type present. Alternatively, the unpurified bone marrow cells have undergone expansion to increase the proportion of a particular cell type present.

In another embodiment of the invention, the bone marrow cells have undergone purification for a particular cell type, for example to increase the proportion of bone marrow stem cells present. In one embodiment of the invention the bone marrow stem cells which are used in the first aspect of the invention are bone marrow stem cells. Techniques for obtaining a purified cell population will be well known to those skilled in the art.

Preferably, the purified bone marrow cells have undergone expansion (either before or after purification; preferably after purification). In this way increased numbers of a particular cell type present may be obtained.

In a second aspect of the present invention there is provided a method of generating a tooth progenitor cell, the method comprising incubating bone marrow cells in the presence of oral epithelial inductive signals to produce a tooth progenitor cell, wherein the bone marrow cells have not undergone purification for a particular cell type.

Preferably, the unpurified bone marrow cells have not undergone expansion to increase the proportion of a particular cell type present. Alternatively, the unpurified bone marrow cells have undergone expansion to increase the proportion of a particular cell type present.

Preferably, in the first and second aspects of the invention at least about 100, 500, 1000, 2500, 5000, 7500, 10000 or 15000 bone marrow cells are incubated in the presence of oral epithelial inductive signals.

Methods for obtaining bone marrow cells will be well known to persons skilled in the art.

The bone marrow cells are preferably obtained from a single individual. Alternatively, the bone marrow cells may be obtained from a number of individuals and pooled.

The bone marrow cells may be prepared for the induction/interaction in a number of ways. For example, they may be pelleted to form small aggregates. This may be accomplished by pelleting them onto filters. Such filters may comprise any suitable substrate, such as pregelatinised Millipore filters. For convenience, the filters may be supported by metal grids, for example as described in Ferguson et al. (1998). The bone marrow cells may be pelleted into small holes made in a gel or other suitable semi-solid support. The gel may be a collagen gel. The gel may be Collaborative Biomedical Products' Matrigel or a similar substrate.

Optionally, epithelium may be overlaid onto the bone marrow cells to cover the hole which is then covered with a thin layer of gel and incubated.

Gels used in this manner may themselves be supported by membrane(s) and/or metal grids.

The bone marrow cells are contacted with oral epithelial inductive signals. Preferably, the bone marrow cells are contacted with any combination of one, two, three or all of the following: FGF8, BMP4, SHH and WNTS. As discussed below, the oral epithelial inductive signals may be provided by a variety of means some of which do not require the presence of embryonic oral epithelial cells.

A tooth progenitor cell is one which expresses certain molecular markers characteristic of tooth progenitor cells. For example, a cell would be considered to be a tooth progenitor cell if it expressed one or more tooth mesenchymal cell markers. Examples of such markers include Barx1. Dlx2, Dlx5, Msx1, Pax9, Activin βA, Lhx6, Lhx7 and others. These markers may be detected by any suitable means, such as western blotting, immunofluorescence, radioactive in situ hybridization or other suitable means.

In wild type teeth at the bud stage Barx-1 gene expression is principally found in the molar region of the mandible and maxilla and is present in a broad field of neural crest derived mesenchymal cells rather than being restricted to dental mesenchyme (Ferguson et al., 1998: Tissier-Seta et al., 1995).

Msx-1, Lef-1 and Bmp-4 are expressed in the dental mesenchyme (i.e. the condensing mesenchymal cells associated with invaginating incisor and molar epithelial tooth buds) in response to epithelial signalling (Ferguson et al., 1998; Mackenzie et al., 1991 Kratochwil et al., 1996; Vainio et al., 1993).

Dlx-2 expression is principally found in mesenchymal cells immediately surrounding the epithelial bud, but is also present in the dental epithelium on the buccal side of the buds (Ferguson et al., 1998; Thomas et al., 1995; Qui et al., 1997).

Pax-9, Lhx6 and Lhx7 are expressed in early tooth mesenchyme prior to bud formation and subsequently in condensing mesenchyme at the bud stage (Ferguson et al., 1998; Neubüiser et al., 1997).

Gli-3 is expressed in the mesenchyme from E10.5. At the bud and cap stage Gli-3 expression is slightly more localised than Par-9 expression, and is concentrated in the dental papilla and dental follicle (Ferguson et al, 1998; Hardcastle and Sharpe, 1998).

Syndecan-1, a cell surface heparin sulphate proteoglycan is transiently expressed in the dental mesenchyme and is thought to regulate dental mesenchymal cell condensation beneath the invaginating dental epithelium (Ferguson et al., 1998; Thesleff et al., 1996).

Tgfβ-1 is found in the dental mesenchyme and weakly in the epithelium of the incisors and only appears in the molars in the dental epithelium at the cap stage (Ferguson et al., 1998; Vaahtokari et al., 1991).

Tgfβ-3 expression is widespread in the mesenchyme of the face, but its expression appears to be substantially absent from the condensing mesenchymal cells immediately adjacent to the epithelial buds of incisors and molars (Ferguson et al., 1998; Chai et al., 1994).

Incubation with the oral epithelial inductive signals is for a time sufficient to produce the tooth progenitor cell. Preferably, this time is at least about 12 hours. Preferably, the time is between 12 and 82 hrs, preferably between 12 and 72 hours. Preferably, the time is between 12 and 24 hours, 12 and 36 hours or 12 and 48 hours.

As discussed in WO 01/60981, the oral epithelial inductive signals may be provided in various ways including: (i) using embryonic oral epithelial cells, (ii) using cells which are not embryonic oral epithelial cells but which express oral epithelial inductive signals and which thereby emulate the signalling characteristics of embryonic oral epithelial cells; and (iii) using purified protein.

In one embodiment of the first and second aspects of the invention, the method comprises incubating the bone marrow cells in the presence of one or more embryonic oral epithelial cells to produce the tooth progenitor cell.

Preferably, the bone marrow cells are incubated in the presence of embryonic oral epithelium.

As established in WO 01/60981, the role of embryonic oral epithelial cells in providing oral epithelial inductive signals may be replaced by using, inter alia, inductive odontogenic cells which emulate the signalling characteristics of embryonic oral epithelium. WO 01/60981 discloses that odontogenic epithelial cells may be produced from cultured cells which may be engineered to possess characteristics of embryonic oral epithelium, thereby allowing replacement of embryonic oral epithelium with engineered epithelium. Examples of cells which may replace the role of embryonic oral epithelial cells in tooth progenitor production are provided in WO 01/60981 and include immortalised cell lines (e.g. epithelial cells derived from immortalised lines of tooth epithelial cells) and ES cell-derived (i.e. cultured cell derived) epithelial cells.

Accordingly, in an alternative embodiment of the first and second aspects of the invention, the bone marrow cells are incubated in the presence of one or more inductive odontogenic cells which emulate the signalling characteristics of embryonic oral epithelial cells to produce the tooth progenitor cell.

The inductive odontogenic cells may be produced from non-oral epithelial cells (e.g. epithelial cells derived from immortalised lines of tooth epithelial cells). Preferably, the odontogenic cells are produced from an immortalised cell line or a stem cell (e.g. ES cell).

The inductive odontogenic cells preferably express one, two, three, four or all of the following: FGF8, BMP4, SHH, Pitx2 and Islet1.

As discussed in WO 01/60981, molecular markers may be analysed to determine whether the signalling properties of early oral epithelium are well established. For instance, expression of FGF8, BMP4, SHH and Pitx2 (the earliest marker of oral epithelium) may be analysed to determine which cells are likely to be able to replace oral epithelial cells. Methods for testing the odontogenic inducing capacity of cell lines are also disclosed in WO 01/60981.

As discussed in WO 01/60981, if the epithelial cells do not properly induce odontogenesis the expression of inductive signalling molecules (FGF8, BMP4, SHH etc.) may be assayed in collagen explant cultures and any missing signals are replaced either by purified proteins on beads or by electroporation of gene expression constructs.

The combination of secreted signals necessary to induce odontogenesis in bone marrow cells may alternatively be provided using purified protein such as by using the bead delivery system as described in WO 01/60981.

Accordingly, in another embodiment of the first and second aspects of the invention the bone marrow cells may be incubated in the presence of protein-containing beads or protein-coated beads to provide oral epithelial inductive signals to produce the tooth progenitor cell. Persons skilled in the art will readily be able to devise suitable concentrations of the proteins.

Once a tooth progenitor cell has been generated, odontogenic inducing capacity resides in the tooth progenitor cell and naive epithelial cells respond to signals from the tooth progenitor cell and allows tooth development. If the growth medium used in the cultures does not contain the factors required for the production of an odontogenic epithelium, the culture media may be supplemented with the necessary factors.

Advantageously, tooth progenitor cells according to the second aspect of the invention may be used for the production of tooth primordia, or more fully developed teeth.

The term "tooth primordia" is well known in the art and refers to structures that can develop into fully-formed teeth.

Incubation of the tooth progenitor cell in the presence of one or more epithelial cells is for a time sufficient to produce a tooth primordium. Preferably, this time is at least about 12 hours. Preferably, the tooth progenitor cell is incubated in the presence of oral epithelium.

Preferably, the one or more epithelial cells are oral epithelial cells; embryonic epithelial cells; oral, embryonic epithelial cells; or are epithelial cells derived from stem cells (embryonic stem (ES) cells or adult stem cells) or an immortalised cell line.

A third aspect of the present invention provides a tooth progenitor cell obtainable by a method according to the second aspect of the invention.

A fourth aspect of the present invention provides a tooth primordium obtainable by a method according to the first aspect of the invention.

The tooth primordia of the first aspect of the invention can be cultured in vitro allowing a variety of manipulation studies including introduction of genes and/or proteins and tissue recombinations. Most significantly, manipulated tooth primordia can be transferred to renal capsules of adult animals (such as humans and mice) to produce conditions for development of adult teeth.

A fifth aspect of the present invention provides a method for generating a tooth the method comprising:
  i) providing a tooth primordium produced by a method according to the first aspect of the invention;
  ii) implanting the tooth primordium into a mammalian kidney or into a space in the oral cavity and allowing the tooth primordium to develop into a tooth.

Preferably, the method of the fifth aspect of the invention is carried out on an individual in need of tooth replacement.

Preferably, the method of the fifth aspect of the invention is carried out on a human patient.

A sixth aspect of the present invention relates to the use of a tooth primordium according to the first aspect of the invention in the manufacture of a medicament for generating a tooth. Preferably, the tooth primordium is used in the manufacture of a medicament for generating a tooth in a subject in need of tooth replacement, preferably a human patient.

Preferably, the methods of the present invention are carried out with human or murine cells.

The present invention may be used for tooth replacement, particularly for murine or human tooth replacement. It is known that embryonic tooth primordia can develop and grow normally in the adult environment, for example using renal transfers (1,4). It seems that sites such as the adult kidney and eye provide a suitable environment largely by allowing an adequate blood supply.

In addition to being able to develop a series of procedures to allow tooth replacement it is desirable that the tooth that develops in situ is of the correct shape and size. A number of the genes that determine tooth shape are known, and by manipulation of these genes it is possible to change tooth shape (1, 4, 7, 8). Similarly, it is shown experimentally that modulation of signalling events leads to alteration of tooth size.

For example, inhibition of Wnt signalling leads to the development of smaller teeth (9). These observations could be advantageously employed in the methods of the present invention.

The methods of the present invention may be advantageously applied to the replacement of the embryonic environment usually required for tooth development by an adult environment, such as via implantation of tooth progenitor cells or structures resulting therefrom into an adult jaw for development. Teeth produced/transplanted according to the present invention continue to grow and develop when implanted into the jaw bone, and become attached thereto.

It is envisaged that the present invention provides for cells to be directed to follow an odontogenic pathway in culture and subsequently develop into mature teeth when implanted into mammalian jaw or kidney.

It is an advantage of the present invention that bone marrow cells can be programmed by exposure to odontogenic signals (eg. from oral epithelium) in culture to subsequently form teeth on implantation (eg. renal implantation, or implantation into jaw).

It is an advantage of the present invention that tooth primordia attach and develop successfully following implantation into the jaw.

Epithelial Markers

Examples of such markers include Pitx2, p21, Wnt7b and others. These markers may be detected by any suitable means, such as western blotting, immunofluorescence, radioactive in situ hybridisation or other suitable means.

Genes known to be expressed in tooth germ epithelium include Bmp-4, Sonic hedgehog (Shh), CD44, FGF8, Pitx2 and Otlx-2 genes.

In wild-type embryos, Bmp-4 is initially expressed in the dental epithelium, but expression shifts to the mesenchyme around the tooth buds from E13.5 (Aberg et al., 1997). At E13.5 mesenchymal Bmp-4 expression is found only in lower incisors, which are the most advanced developmentally at this stage, whereas expression persists in the epithelium of upper incisors and molars (Ferguson et al., 1998).

Shh is expressed in the epithelial thickening of early tooth germs and is thought to be an important component of the signals that pass from the epithelium to the underlying mesenchyme at this early stage, inducing gene expression in the mesenchyme (Bitgood and McMahon, 1995; Thesleff and Sharpe, 1997). At later stages, Shh is down-regulated but transcripts reappear in the epithelial cells that constitute the enamel knot, a transient signalling centre that arises in the dental epithelium at the late bud stage of tooth development (Ferguson et al., 1998; Vaahtokari et al, 1996).

CD44 and Otlx-2 are expressed more widely in the oral epithelium than Shh (Ferguson et al., 1998; Mucchielli et al, 1997). CD44 encodes the hyaluronan receptor and Otlx-2 is the murine homologue of the human gene which when mutated, causes the disease known as Rieger syndrome in which teeth are absent (Semina et al; 1996).

Follistatin is an activin-binding protein that has been shown to inhibit the activity of activin (Michel et al., 1993; De Winter et al, 1996). The expression pattern of Follistatin may be examined by in situ hybridisation analysis (Ferguson et al., 1998).

Follistatin expression is found in tooth germ epithelial cells immediately adjacent to activin expressing cells from El1.5. At later stages, follistatin transcripts are restricted to the columnar-shaped cells that form the outermost layer of the epithelial bud, while the central core of epithelial cells are follistatin-negative (Ferguson et al., 1998). Follistatin is therefore expressed in the tooth epithelium adjacent to and in a complementary pattern to activin in the tooth mesenchyme.

EXAMPLES

The present invention will now be described by way of example, in which reference is made to:

Example 1

Derivation & Culture of the Murine Bone Marrow Cells

Bone marrow cells were collected from tibiae and femora of 6-9-week-old female wild-type mice. Five mice were killed by cervical dislocation, and femurs and tibiae were aseptically removed and dissected free of adherent tissue. Both ends of the bone were cut, and the bone cavity was flushed out with culture medium slowly injected at the end of the bone using a sterile 21-gauge needle. Bone marrow cells were subsequently suspended in minimal essential medium (MEM; Sigma Chemical Co., St. Louis, Mo.) containing 10% heat-inactivated foetal bovine serum (FBS; GIBCO BRL, Grand Island, N.Y., USA) and were maintained for 14 days in a 75-cm2 tissue flask. The medium was changed after 3 days and then subsequently every 2 days.

Example 2

Preparation of Oral Epithelium

Mandibles of embryos were dissected out in DMEM with glutamax-1. The epithelium was isolated following incubation in a solution of Dispase (GIBCO BRL) made up in calcium- and magnesium-free PBS at 2 U/ml for 10-15 min at 37° C. After incubation the tissues were washed in DMEM with 10% FCS, and the epithelium was mechanically separated using fine tungsten needles.

Example 3

Co-Culture of Bone Marrow Cells with Oral Epithelium

The bone marrow cells were cultured as described in Example 1 and removed by brief exposure to trypsin, collected in medium, centrifuged, washed again in medium and centrifuged twice. The cells were then counted and resuspended at two million cells in 50-100 μl medium. These stem cells were then centrifuged for 10-20 sec at 10.000 g to form a pellet which was then placed on a transparent Nucleopore membrane filters (0.1-μm-pore diameter; Costar), pre-soaked in 1% gelatin solution. Excess medium was removed from around the pellet. Cell pellets were incubated on the membrane filter supported by a metal grid for 10-15 min at 37° C. following the Trowel technique as modified by Saxén (Trowel 1959, Saxén 1966) at 37° C. with an atmosphere of 5% CO2/95% air and 100% humidity.

3-4 epithelia, prepared as described in Example 2, were then placed over the cell pellet. The co-cultures were incubated for a further 3 days.

Example 4

Renal Capsule Implantation

The co-cultures of bone-marrow cells and oral epithelium, described in Example 3, were surgically implanted under the renal capsule of male adult mice and cultured for a further 10 days to allow tooth development. At the end of this period, the mice were sacrificed and the renal implant site examined for gross morphology. Ectopic tooth development was confirmed by decalcification of the tissue, wax embedding, staining with haematoxylin & eosin and histological examination.

Results

Figure 1:
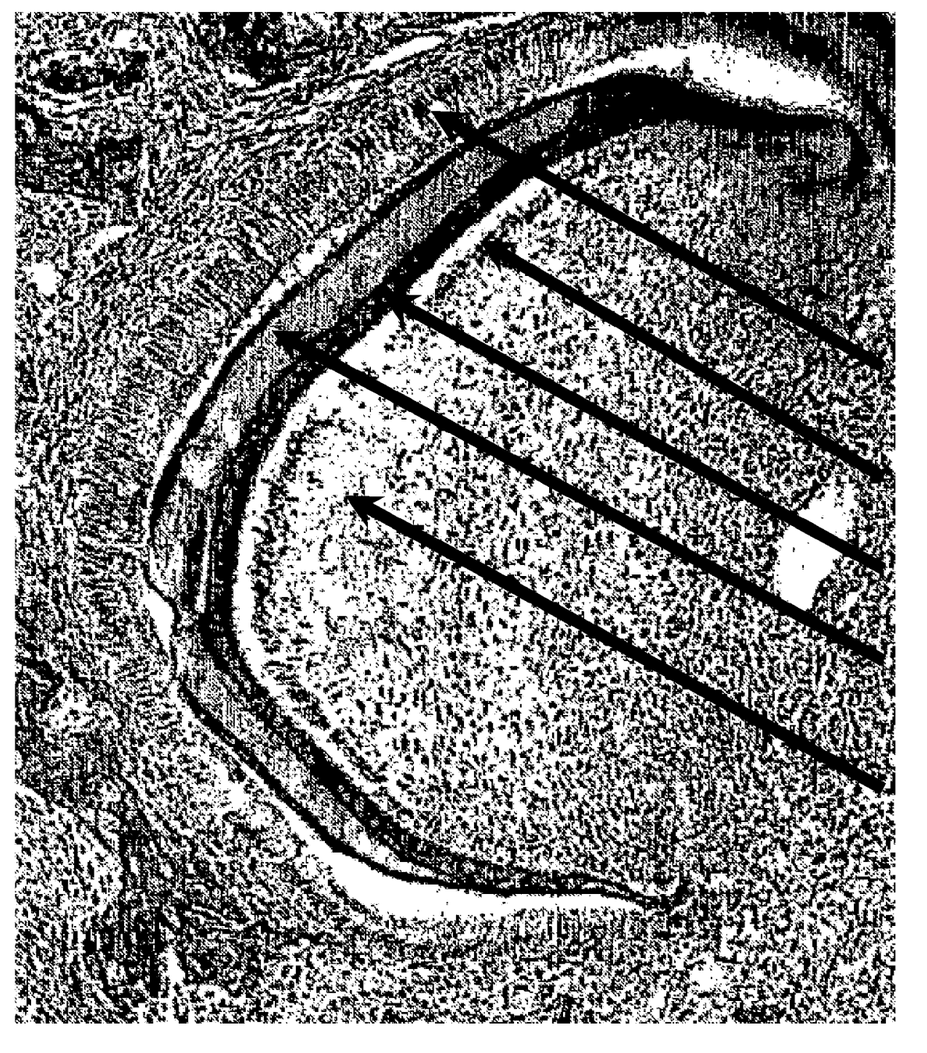
FIG. 1: Tooth structure observed at the implantation site.

Tooth structures were observed at the implantation site. An example is shown in FIG. 1. From upper arrow to lower arrow, the tooth structures shown in FIG. 1 are Ameloblasts, Dentin, Predentin, Odontoblasts and Dental Pulp.

Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

All documents mentioned herein are incorporated herein in their entirety.

Aberg, T., Wozney, J. and Thesleff, I. 1997. Expression patterns of BMPs in the developing mouse tooth suggest roles in morphogenesis and cell differentiation. Dev. Dyn. 210 383-396.

Asashima, M., Nakano, H., Shimada, K., Kinoshita, K., Ishii, K., Shibai, H., and Ueno, N. 1990. Mesodermal induction in early amphibian embryos by activin A (erythroid differentiation factor). Roux's Arch. Dev. Biol. 198: 330-335.

Bitgood, M. J. & McMahon, A. P. 1995. Hedgehog and Bmp genes are coexpressed at many diverse sites of cell-cell interaction in the mouse embryo. Dev. Biol. 172: 126138.

Chai, Y., Mah, A., Crohin. C. Groff, S., Bringas, P., Jr., Le, T., Santos, V. and Slavkin, H. C. 1994. Specific transforming growth factor-beta subtypes regulate embryonic mouse Meckel's cartilage and tooth development. Dev. Biol. 162: 85-103.

Chen, Y., Bei, M., Woo, I., Satokata, I. and Maas, R. 1996. Msx1 controls inductive signalling in mammalian tooth morphogenesis. Development 122: 3035-3044.

Conlon, F. 1994. A primary requirement for Nodal in the formation and maintenance of the primitive streak in the mouse. Development 120: 1919-1928.

Crossley, P. H. and Martin, G. R. 1995. The mouse Fgf8 gene encodes a family of polypeptides and is expressed in regions that direct outgrowth and patterning in the developing embryo. Development 121, 439-451.

De Winter, J. P., Ten Dijke P., De Vries, C. J. M., Van Acterberg, T. A. E., De Waele, P., Huylebroeck, D., Verschueren, K. and Van den Eijnden-van Raaij, A. J. M. 1996. Follistatins neutralise activin bioactivity by inhibition of activin binding to its type II receptors. Mol. Cell Endocrinol. 116: 105-114.

Dohrmann, C. E. Hemmati-Brivanlou, A., Thomsen, G. H. and Fields, A. 1993. Expression of activin mRNA during early development in *Xenopus laevis*. Dev. Biol. 157: 474-483.

Dyson, S. and Gurdon, J. B. 1997. Activin signalling has a necessary function in *Xenopus* early development. Clzrr. Biol. 7: 81-84.

Fainsod, A., Deissler, K., Yelin, R., Marom, K., Epstein. M., Pillemer, G., Steinbeisser, H. and Blum, M. 1997. The dorsalizing and neural inducing gene follistatin is an antagonist of BMP-J. Alech. Dev. 63: 39-50.

Feijen, A., Goumans, M. J. and van den Eijnden-van Raaij. 1994. Expression of activin subunits, activin receptors and follistatin in postimplantation mouse embryos suggests specific developmental functions for different activins. Development 120: 3621-3637.

Ferguson C. A., Tucker A. S., Christiensen L., Lau A. L., Matzuk M. M. and Sharpe P. T. 1998. Activin is an essential early mesenchymal signal in tooth development that is required for patterning of the murine dentition. Genes Dev. 12: 2636-2649

Green, J. B. A., and Smith J. C. 1990. Graded changes in dose of a *Xenopus* activin A homologue elicit stepwise transitions in embryonic cell fate. Nature 347: 391-394.

Green, J. B. C., New, H. V., and Smith, J. C. 1992. Responses of embryonic *Xenopus* cells to activin and FGF are separated by multiple dose thresholds and correspond to distinct axes of the mesoderm. Cell 71: 731-739.

Grigoriou, M., Tucker, A. S., Sharpe, P. T. and Pachnis, V. 1998. Expression and regulation of Lhx6 and Lhx7, a novel subfamily of LIM homeodomain encoding genes, suggests a role in mammalian head development. Development, in press.

Hardcastle, Z., Mo, R., Nui, C.-c. and Sharpe, P. T. 1998. The Shh signalling pathway in tooth development: defects in Gli2 and Gli3 mutants. Development. In press.

Heikinheimo, K., Begue-Kirn, C., Ritvos, O., Tuuri, T. and Ruch, J. V. 1997. The activin-binding protein follistatin is expressed in developing murine molar and induces odontoblast-like cell differentiation in vitro. J. Dent. Res. 76: 1625-1636.

Heikinheimo, M., Lawshe, A., Shackleford, G. M., Wilson, D. B. and MacArthur, C. A. 1994. Fgf-8 expression in the post-gastrulation mouse suggests roles in the development of the face, limbs and central nervous system. Mach. Dev. 48: 129-138.

Hemmati-Brivanlou, A., and Melton, D. A. 1992. A truncated activin receptor dominantly inhibits mesoderm induction and formation of axial structures in Xenopars embryos. Vature 359: 609-614.

Hemmati-Brivanlou, A., and Melton, D. A. 1994. Inhibition of activin receptor signalling promotes neuralization in *Xenopus*. Cell 77: 273-281.

Hemmati-Brivanlou, A., Kelly, O. G., and Melton, D. A. 1994. Follistatin, an antagonist of activin, is expressed in the Spemann Organiser and displays direct neuralizing activity. Cell 77: 283-295.

Iseki, S., Araga, A., Ohuchi, H., Nohno, T., Yoshioka, H., Hayashi, F. and Noji, S. 1996. Sonic hedgehog is expressed in epithelial cells during development of whisker, hair, and tooth. Biochem. Biophys. Res. Commun. 218: 688-693.

Kettunen, P. and Thesleff, 1. 1998. Expression and function of FGFs-4,-8, and -9 suggest functional redundancy and repetitive use as epithelial signals during tooth morphogenesis. Dev. Dyn. 211: 256-268.

Kollar, E. J. and Baird G. R. 1969. The influence of the dental papilla on the development of tooth shape in embryonic mouse tooth germs. J. Embryol. Exp. Morph. 21: 131-148.

Kratochwil, K., Dull, M., Fari-as, I., Galceran, J. and Grosschedl, R. 1996. Lef1 expression is activated by BMP-4 and regulates inductive tissue interactions in tooth and hair development. Genes Dev. 10: 1382-1394.

Lumsden A G. 1988. Spatial organisation of the epithelium and the role of neural crest cells in the initiation of the mammalian tooth germ. Development 103: 155-169.

Mackenzie, A., Leeming, G. L., Jowett. A. K., Ferguson, M. W. J. and Sharpe, P. T.1991. The homeobox gene Hor-7.1 has specific regional and temporal expression patterns during early murine craniofacial embryogenesis, especially tooth development in vivo and in vitro. Development 111: 269-285.

Matzuk, M. M., Kumar, T. R., Vassalli, A., Bickenbach, J. R., Roop, D. R., Jaenisch, R. and Bradley, A. 1995a. Functional analysis of activins during mammalian development. Nature 374: 354-356.

Matzuk, M. M., Kumar, and Bradley, A. 1995b. Different phenotypes for mice deficient in either activins or activin receptor type 11. Nature 374: 356-360.

Matzuk, M. M., Lu, N., Vogel, H., Selheyer, K., Roop, D. R., and Bradley, A. 1995c.

Multiple defects and perinatal death in mice deficient in follistatin. Nature 374: 360363.

Michel, U., Farnworth, P. and Finlay, J. P. 1993. Follistatins: more than folliclestimulating hormone suppressing proteins. Mol. Cell Endocrinol. 91: 1-11.

Mina M., and Kollar E. J. 1987. The induction of odontogenesis in non-dental mesenchyme combined with early murine mandibular arch epithelium. Arch. Oral. Biol. 32: 123-127.

Mucchielli, M., Mitsiadis, T. A., Raffo, S., Brunet, J., Proust, J. and Goridis, C. (1997) Mouse Otlx2/RIEG expression in the odontogenic epithelium precedes tooth iniation and requires mesenchymal derived signals for its maintenance. Dev. Biol. 189: 275284.

Nakamura. T., Takio, K., Eto, Y., Shibai, H., Titani, K. and Sugino, H.1990. Activinbinding protein from rat ovary is follistatin. Science 247: 836-838.

Neubuser, A., Peters, H., Balling, R. and Martin, G. R. 1997. Antagonistic interactions between FGF and BMP signalling pathways: a mechanism for positioning the sites of tooth formation. Cell. 90: 247-255.

Page, K. M. 1990. Bone. In Theory and Practice of Histological techniques. Third Edition. (ed J. D. Bancroft and A. Stevens), pp. 309-341. Churchill Livingstone, Edinburgh, London, Melbourne and New York.

Pownall, M. E., Tucker, A. S., Slack, J. M. W. and Isaacs, H. V. 1996. eFGF, Xcad3 and Hox genes form a molecular pathway that establishes the anteroposterior axis in *Xenopus*. Development 122: 3881-3892.

Qiu, M., Bufone, A., Ghattas, I., Menses, J. J., Sharpe, P. T., Presley, R., Pedersen, R. A.& Rubenstein, J. L. R. 1997. Role of Dlx-1 and -2 in proximodistal patterning of the branchial arches: mutations alter morphogenesis of proximal skeletal elements derived from the first and second branchial arches. Dev. Biol. 185: 165-184.

Roberts, V. J. and Barth, S. L. 1994. Expression of messenger ribonucleic acids encoding the inhibin/activin system during mid- and late-gestation rat embryogenesis. Endocrinology 128: 914-923.

Roberts, V. J., Sawchenko, P. E. and Vale, W. W. 1991. Expression of inhibin/activin subunit messenger ribonucleic acids during rat embryogenesis. Endocrinology 128: 3122-3129.

Saxen, L. 1966. The effect of tetracyclin on osteogenesis in vitro. J. Exp. Zool. 162: 269-294.

Satokata, I. & Maas, R. 1994. Msx-I deficient mice exhibit cleft palate and abnormalities of craniofacial and tooth development. Nature Genet. 6: 348-356.

Semina, E. V., Reiter, R., Leysens, N. J., Alward, W. L., Small, K. W., Datson, N. A., Siegel-Bartelt, J., Bierke-Nelson, D., Bitoun, P., Zabel, B. U., Carey, J. C. and Murray, J. C. 1996. Cloning and characterization of a novel bicoid-related homeobox transcription factor gene, RIEG, involved in Rieger syndrome. Nat. Genet. 14: 392399.

Thesleff, 1. and Sharpe, P. T. 1997. Signalling networks regulating dental development. Mech. Dev. 67: 111-123.

Thesleff, I, Vaahtokari, A, & Partanen, A-M. 1995. Regulation of organogenesis. Common molecular mechanisms regulating the development of teeth and other organs. Int. J. Dev. Biol. 39: 35-50.

Thesleff, I., Vaahtokari, A., Vainio, S. and Jowett, A. 1996. Molecular mechanisms of cell and tissue interactions during early tooth development. Anatomical Record 245: 151-161.

Thomas, B. T., Porteus, M. H., Rubenstein, J. L. R. and Sharpe, P. T. 1995. The spatial localisation of Dlx-2 during tooth development. Conn. Tiss. Res. 32: 27-34.

Thomas, B. L., Tucker, A. S., Qui, M., Ferguson, C. A., Hardcastle, Z., Rubenstein, J. L. R. and Sharpe, P. T. 1997. Role of Dlx-1 and Dlx-2 genes in patterning of the murine dentition. Development 124: 4811-4818.

Thomsen, G., Woolf, T., Whitman, M., Sokol, S., Vaughan, J., Vale, W., and Melton, D. A. 1990. Activins are expressed early in *Xenopus* embryogenesis and can induce axial mesoderm and anterior structures. Cell 63: 485-493.

Tissier-Seta, J. P., Mucchielli, M. L., Mark, M., Mattei, M. G., Goridis, C. and Brunet, J. F. 1995. Barx1, a new mouse homeodomain transcription factor expressed in craniofacial ectomesenchyme and the stomach. Mech. Dev. 51: 3-15.

Trowell, O. A. 1959. The culture of mature organs in a synthetic medium. Exp. Cell Research 16: 118-147.

Vaahtokari, A., Vainio, S. and Thesleff, 1. 1991. Associations between transforming growth factor beta 1 RNA expression and epithelial-mesenchymal interactions during tooth morphogenesis. Development 113: 985-994.

Vaahtokari, A., Aberg, T., Jernvall, J., Keranen, S. and Thesleff, I. 1996 The enamel knot as a signalling center in the developing mouse tooth. Azfech. Dev. 54: 39-43.

Vainio, S., Karavanova, I., Jowett, A. and Thesleff, 1. 1993. Identification of BMP-4 as a signal mediating secondary induction between epithelial and mesenchymal tissues during early tooth development. Cell 75: 45-58.

Vale, W. W., Hseuh, A, Rivier, C. and Yu, J. 1990. The inhibin/activin family of hormones and growth factors. In: Peptide growth factors and their receptors II. (ed M. B. Sporn and A. B. Roberts), pp. 211-248. Springer-Verlag, Berlin van Genderen, C., Okamura, R. M., Fari-as, I., Quo, R. G., Parslow, T. G., Bruhn, L. and Grosschedl, R. 1994. Development of several organs that require inductive epithelial-mesenchymal interactions is impaired in LEF-1-deficient mice. Genes Dev. 8: 2691-9703.

Wilkinson, D. G. 1995. In Situ Hybridisation, A practical approach. IRL Press, Oxford, UK.

Yamashita, H., ten Dijke, P., Huylebroeck, D., Sampath. T. K., Andries, M., Smith, J. C., Heldin, C.-H. and Miyazono, K. 1995. Osteogenic protein-1 binds to activin type II receptors and induces certain activin-like effects. J. Cell. Biol. 130: 217-226.

Phinney D G. J Cell Biochem Suppl 2002; 38:7-12

Krause D S. Gene Ther 2002 June; 9(11):754-8

Bianco P, Riminucci M, Gronthos S, Robey P G. Stem Cells 2001; 19(3):180-92

Prockop D J, Azizi S A, Colter D, Digirolamo C, Kopen G, Phinney D G. Biochem Soc Trans 2000; 28(4):341-5

Van Damme A, Vanden Driessche T, Collen D, Chuah MK. Curr Gene Ther 2002 May; 2(2): 195-209

Ballas C B, Zielske S P, Gerson S L. J Cell Biochem Suppl 2002; 38:20-8

Ito T, Suzuki A, Okabe M, Imai E, Hori M. Exp Nephrol 2001; 9(6):444-50

Minguell J J, Erices A, Conget P. Exp Biol Med (Maywood) 2001 June; 226(6):507-20

Koc O N, Lazarus H M. Bone Marrow Transplant 2001 February; 27(3):235-9

Caplan A I, Bruder S P. Trends Mol Med 2001 June; 7(6): 259-64

Prockop D J. Science 1997 Apr. 4; 276(5309):71-4

Young, C. S., Terada, S., Vacanti, J. P., Honda, M., Bartlett, J. D., Yelick, P. C. (2002) Tissue engineering of complex tooth structures on biodegradable polymer scaffolds. J. Dent. Res. 81, 695-700.

NUMBERED REFERENCES

1. Tucker A S, Matthews K L and Sharpe P T. (1998). Science 282, 1136-1138
2. Lumsden A S G (1988) Development 103, 122-169
3. Thesleff I and Sharpe P T (1997) Mechs. Dev. 67, 111-123 4.
4. Ferguson C A, Tucker A S, Christensen L, Lau A L, Matsuk M M and Sharpe P T (1998) Genes Dev. 12, 2636-2649
5. Bagutti C, Wobus A M, Fassler R and Watt F M (1996) Dev. Biol. 179, 184-196
6. Rathjen J, Lake J-A, Bettess M D, Washington J M, Chapmen G and Rathjen P D (1999) J. Cell Sci. 112, 601-612 7.
7. Thomas B L, Tucker A S, Qiu M, Ferguson C A, Hardcastle Z, Rubenstein J L R and Sharpe PT (1997). Development 124, 4811-4818
8. Ferguson C, Tucker A S and Sharpe P T (2000) Development in press.
9. Sarkar L and Sharpe P T (2000) J. Dent. Res. in press.
10. Satokata I and Maas R (1994) Nat. Gen. 6, 348-356
11. Hardcastle, Z, Mo, R., Hui, C-c and Sharpe P. T. (1998) Development 125, 2803 2811
12. Lu M-F, Pressman C. Dyer R, Johnson R and Martin J F (1999) Nature 401, 276 278
13. Lin C R, Kioussi C, O'Connell S, Briata P, Szeto D, Liu F, Izpisua-Belmonte J C and Rosenfeld M G (1999) Nature 401, 279-282
14. Gage P J, Suh H and Camper S A (1999) Development 126, 4643-4651

The invention claimed is:

1. An in vitro method of generating a tooth progenitor cell, the method comprising the steps of:
    a) obtaining human or mouse bone marrow cells comprising mesenchymal stem cells, wherein the bone marrow cells have not undergone expansion to increase the proportion of a particular cell type present, and
    b) incubating the human or mouse bone marrow cells comprising mesenchymal stem cells in the presence of an embryonic oral epithelial cell for at least twelve hours, wherein when the human or mouse bone marrow cells comprising mesenchymal stem cells and embryonic oral epithelial cell co-culture is surgically implanted into a subject, the tooth progenitor cell:
    i) differentiates into an odontoblast, and
    ii) forms a tissue selected from the group consisting of dental pulp, predentin, dentin and combinations thereof.

* * * * *